(12) United States Patent
Schipper et al.

(10) Patent No.: US 9,060,715 B2
(45) Date of Patent: Jun. 23, 2015

(54) NEBULIZER

(75) Inventors: Alphonsus Tarcisius Jozef Maria Schipper, Eindhoven (NL); Michael James Robbert Leppard, Hunston (GB); Jonathan Stanley Harold Denyer, Chichester (GB); Tony Dyche, Hayling Island (GB); Klaas Jacob Lulofs, Eindhoven (NL); Jaap Roger Haartsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 335 days.

(21) Appl. No.: 13/379,841

(22) PCT Filed: Jul. 20, 2010

(86) PCT No.: PCT/IB2010/053299
§ 371 (c)(1),
(2), (4) Date: Dec. 21, 2011

(87) PCT Pub. No.: WO2011/010282
PCT Pub. Date: Jan. 27, 2011

(65) Prior Publication Data
US 2012/0285447 A1 Nov. 15, 2012

(30) Foreign Application Priority Data

Jul. 22, 2009 (EP) .................................. 09166078

(51) Int. Cl.
*A61M 15/00* (2006.01)
*A61B 5/11* (2006.01)
(Continued)

(52) U.S. Cl.
CPC ......... *A61B 5/1117* (2013.01); *Y10T 29/49128* (2015.01); *Y10T 29/49117* (2015.01);
(Continued)

(58) Field of Classification Search
CPC .... A61B 5/1117; A61B 5/6831; A61B 5/681; G08B 21/0446; A61M 15/00; A61M 15/001; A61M 15/0028; A61M 15/0065; A61M 15/0085; A61M 15/0091; A61M 15/0015; A61M 16/10; A61M 16/16; A61M 16/14; A61M 16/1065; A61M 15/0018; A61M 15/02; A61M 15/008; A61M 11/007; A61M 15/005; A61M 15/0048; A61M 11/00; A61M 15/025; G01P 5/10; G01P 5/12; G01P 13/006; B06B 1/02; B06B 1/0223; B05B 17/06; B05B 17/04; B05B 17/0638; B05B 17/0669; B05B 17/0676; B05B 17/0661; B05B 12/08; B05B 17/0646; B05B 17/0684; B05B 1/08; B05B 5/00; B05B 11/309; B05B 11/3094; B41J 2/025; B41J 2/015; B41J 2/04; C25D 1/08
USPC ............ 128/200.11–200.24, 203.12, 203.13, 128/203.15, 204.18, 204.23, 205.23; 239/102.2, 335, 338, 505

See application file for complete search history.

(56) References Cited

U.S. PATENT DOCUMENTS 5,133,343 A   7/1992  Johnson, IV et al.
5,134,995 A * 8/1992  Gruenke et al. ......... 128/204.23
(Continued)

FOREIGN PATENT DOCUMENTS

WO    2011010260 A1    1/2011

OTHER PUBLICATIONS http://www.activaero.de; Home—Activaero, Downloaded Sep. 24, 2014, 1 Page.
(Continued)

*Primary Examiner* — Annette Dixon

(57) ABSTRACT

A nebulizer comprises a head detachably coupled to a body. The head comprises the nebulizer, an air channel and a flow sensor. A nebulized liquid is released in an air channel that ends in a mouth piece through which a user inhales and exhales. The inhaling and exhaling causes a flow in the air channel which is detected with the flow sensor. The nebulizer is controlled by controls and sensors included in the body.

31 Claims, 3 Drawing Sheets

Figure 1:
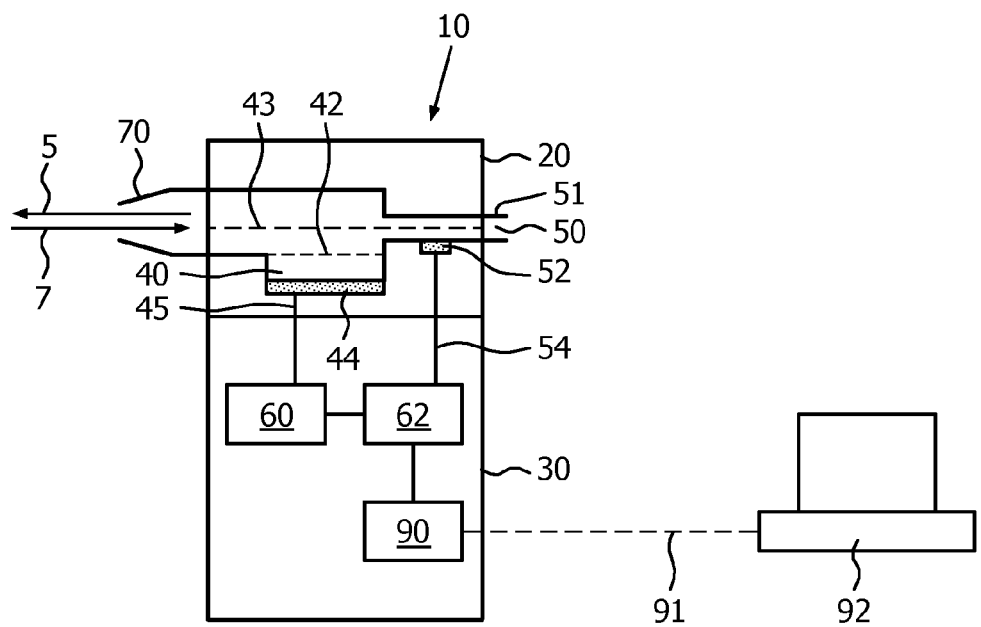
Figure 2:
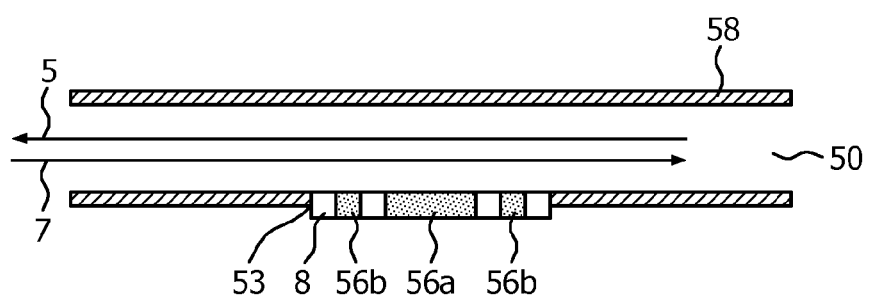
Figure 3:
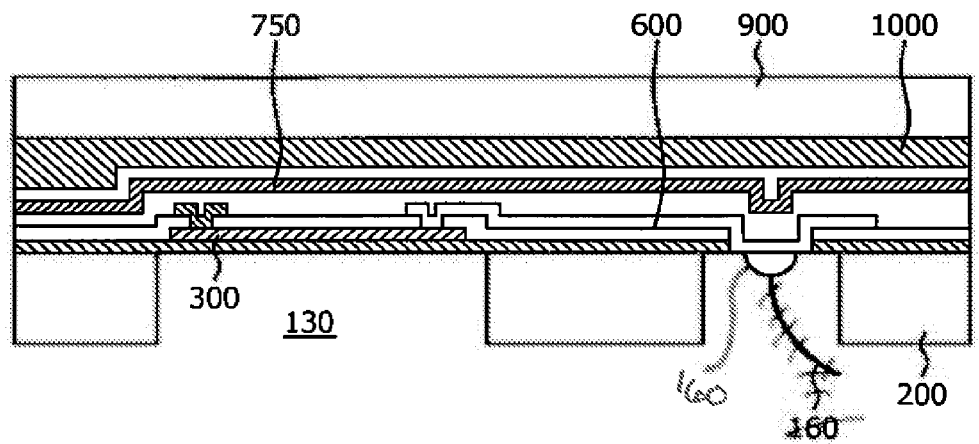
Figure 4:
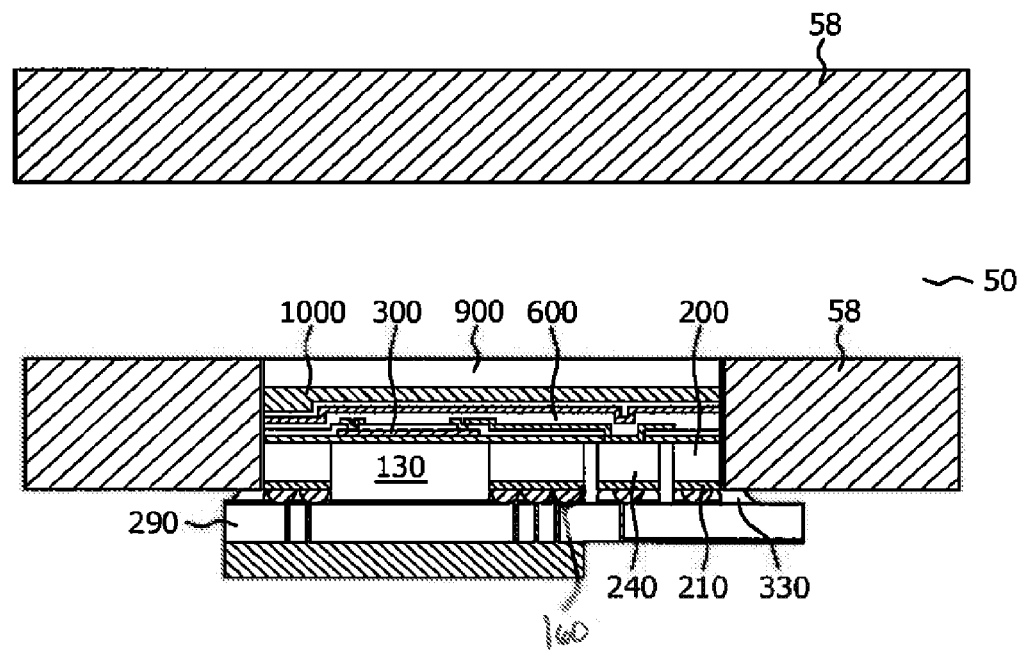

(51) Int. Cl.
*A61B 5/00* (2006.01)
*G01P 5/10* (2006.01)
*G01P 5/12* (2006.01)
*G01P 13/00* (2006.01)
*G08B 21/04* (2006.01)
*A61M 5/168* (2006.01)
*A61M 16/00* (2006.01)

(52) U.S. Cl.
CPC ............... *A61B5/681* (2013.01); *A61B 5/6831* (2013.01); A61B 2562/0219 (2013.01); A61B 2562/0271 (2013.01); *A61M 5/16886* (2013.01); *A61M 15/00* (2013.01); A61M 2016/0021 (2013.01); A61M 2205/332 (2013.01); A61M 2205/3334 (2013.01); A61M 2205/3368 (2013.01); A61M 2205/3375 (2013.01); *G01P 5/10* (2013.01); *G01P 5/12* (2013.01); *G01P 13/006* (2013.01); *G08B 21/0446* (2013.01)

(56) References Cited

U.S. PATENT DOCUMENTS

| | | | | |
|---|---|---|---|---|
| 5,392,768 | A | * | 2/1995 | Johansson et al. ........ 128/200.14 |
| 5,743,250 | A | * | 4/1998 | Gonda et al. ............. 128/200.14 |
| 6,205,999 | B1 | * | 3/2001 | Ivri et al. ................. 128/200.22 |
| 6,328,033 | B1 | * | 12/2001 | Avrahami ................ 128/203.15 |
| 6,349,724 | B1 | * | 2/2002 | Burton et al. ............ 128/204.18 |
| 2004/0031331 | A1 | | 2/2004 | Blakley et al. |
| 2006/0048772 | A1 | * | 3/2006 | Borgschulte ............. 128/200.14 |
| 2007/0107725 | A1 | | 5/2007 | Addington et al. |
| 2008/0017198 | A1 | | 1/2008 | Ivri |
| 2012/0285447 | A1 | | 11/2012 | Schipper et al. |

OTHER PUBLICATIONS http://ineb.respironics.com/AAD.asp., Adaptive Aerosol Delivery (AAD), 2011.

* cited by examiner

NEBULIZER

FIELD OF THE INVENTION

The invention relates to a nebulizer comprising a head and a body, the head being arranged for nebulizing a liquid and being detachably coupled to the body to facilitate cleaning of the head. The invention further relates to a nebulizer system comprising the nebulizer and a personal computer which are coupled for data exchange. The invention further relates to a method of detecting an inhaled or exhaled breath of a person using the nebulizer and to a method of training a person in the use of the nebulizer.

BACKGROUND OF THE INVENTION

Nebulizers are known in the art. See for example http://ineb.respironics.com/ for a nebulizer of the applicant. A nebulizer works most efficient and causes the least environmental pollution when it is breath activated. When working breath activated, aerosol is only delivered during inhalation and not during exhalation. An advanced implementation of breath activated aerosol delivery is known as Adaptive Aerosol Delivery or AAD, see for example http://ineb.respironics.com/AAD.asp.

After use the nebulizer any remaining medicine must be removed and the nebulizer must be cleaned well before it can be used again. For example patients suffering from Cystic Fibrosis are susceptible to infections and any contamination of the nebulizer must be prevented. This requires that all parts that have been in contact with a medication liquid and/or the inhaled or exhaled air must be desinfectable using for example steam cleaning or ethanol immersion.

It is an object of the invention to provide a nebulizer that facilitates an easy and good cleaning

SUMMARY OF THE INVENTION

In one embodiment, the nebulizer comprises a detachable head to enable an easy disinfecting of the head. The body does not require frequent cleaning by, for example, steam cleaning, which enhances the lifetime of the body. By having the sensor included in the head instead of for example having a pressure sensor included in the body and coupled with a separate channel to the air channel, the inhaled and exhaled breath are not in contact with the body. Thus only the nebulizer and the air channel included in the head of the nebulizer are in contact with the liquid, nebulized liquid or the inhaled and exhaled breath of the user. This reduces possible sources of contamination. The controller included in the body controls the nebulizing of the liquid.

The head comprises the medication chamber which may be filled with a liquid, for example a dissolved medication. The vibration source included in the head transfers vibrations to the liquid such that the liquid is ejected through the holes of the mesh to form small droplets in the air channel.

For cleaning, the head may be opened to obtain access to the parts (e.g. the nebulizing means) that may contact the inhaled or exhaled breath, the liquid or the nebulized liquid such as the air channel, the medication chamber, the vibration source and the mesh.

The head and the body may be parts that are coupled using a cable. The cable provides the energy transfer or control signals from the body to the head as well as the signal transfer from the sensing means (e.g. flow sensor or pressure sensor) positioned in the head to a controlling means included in the body. The signal from the sensing means may be an analog or a digital signal. In this embodiment the head is detachable from the body by disconnecting of the cable from for example only the head. This may for example be realized using a plug-socket coupling between the cable and the head. In use the body with the controlling means is for example placed on the table and the cable is connected to the head which is hold by the user. In this embodiment the energy source (e.g. battery) is included in the body resulting in a relative lightweight head.

In another embodiment of the nebulizer the head and the body parts have a shape and/or mechanical interface to enable a direct connection of the head to the body to form one unit that is hold by the user. When the head is clamped to the body also an electrical coupling between the head and the body is established to enable energy transfer from the body to the head and signal transfer from the head to the body.

In a further embodiment the nebulizing of the liquid is dependent on the signal received from the sensing means.

In a further embodiment the sensing means comprises a pressure sensor. The pressure in the air channel drops during an inhalation and increases during an exhalation. The signal of the pressure sensor can therefore be used to distinguish between inhaling and exhaling.

In a further embodiment the sensing means comprises a flow sensor. The flow sensor detects the flow in the air channel. With the signal of the flow sensor inhaling and exhaling can be distinguished.

In yet a further embodiment of the nebulizer the flow sensor is a thermal flow sensor device arranged to sense a flow in the air channel which is caused by the inhaled and exhaled breath of the user. The flow causes a temperature gradient across the surface of the thermal element that is included in the flow sensor device and based on a temperature measurement the flow in the air channel is sensed. For example the thermal element may comprise a heating element with two temperature sensing element at opposing sides of the heating element, and all positioned in a same plane along which a flow caused by the inhaled and exhaled breath passes.

The thermal flow sensor device may comprise an electrically driven thermal element on its front side which faces the interior of the air channel. The inhaled and exhaled breath causes a flow through the air channel that passes the thermal element and causes a temperature gradient which is detected by the thermal flow sensor device and converted to the signal that is used by the nebulizing controlling means which are included in the body.

In yet a further embodiment the thermal flow sensor device or the pressure sensor is built in a wall of the air channel. Because of hygiene the thermal flow sensor device or the pressure sensor may be integrated in the wall thereby obtaining a smooth inner surface of the air channel that may be cleaned easily. For example the wall may have a recess with a shape that matches with the dimensions of the thermal flow sensor device or pressure sensor.

The pressure sensor may comprise an integrated circuit die. In an embodiment the pressure sensor is a MEMS pressure sensor capable of providing a signal that is dependent on the absolute pressure. MEMS or Micro-Electro-Mechanical Systems refers to the integration of mechanical elements, sensors, actuators, and electronics on a common silicon substrate through integrated circuit (IC) process sequences (e.g. CMOS, Bipolar or BICMOS processes). The MEMS pressure sensor comprises a capacitor of which a distance between the plates is dependent on the pressure in the air channel. For example a low pressure causes the distance to increase and the capacitance to decrease. Likewise a high pressure in the channel causes the distance to decrease and the capacitance to increase.

The thermal flow sensor device may comprise an integrated circuit die on which the thermal element is integrated.

In an embodiment of the integrated circuit the die has a component side on which the thermal element is located and a back side on which the bondpads for connecting the thermal element are located. When the thermal flow sensor device is positioned in the recess in the wall the component side of the die faces the interior of the air channel. By having the bondpads accessible from the backside of the integrated circuit die the space needed for the bondpad and any connection to it do not influence the flow of the inhaled and/or exhaled breath along the thermal element. This improves the sensitivity and performance of the thermal flow sensor device.

In a further embodiment of the integrated circuit the heating element is realized as a polysilicon resistor and the temperature sensing elements are realized as a string of polysilicon-metal junctions. The manufacturing of this heating and temperature sensing element requires only a limited number of processing steps while the feature size of the used lithography may be relatively large.

In yet a further embodiment said die is glued with its component side on a thin glass plate. The thickness of the plate is chosen to have a low thermal resistance and provides the die mechanical stability. Bondpads at the backside of the die are obtained using an etching processing step of selected positions of the substrate.

With a heating element flanked by two thermal sensing elements, one at either side, a temperature difference caused by a flow can be measured. The sign (positive or negative) of the measured temperature difference corresponds with the flow. Hence with this simple thermal element an inhaled breath can be distinguished from an exhaled breath, which may be used to obtain AAD.

In yet a further embodiment of the nebulizer the mesh is detachably coupled to the medication chamber. This enables a replacement of the mesh as well as a simple emptying of the medication chamber after use or during cleaning of the head. After frequent use the mesh performance may deteriorate, for example because residues obstruct some percentage of the many small holes of the mesh.

To prevent spillage when only a small amount of medication liquid needs to be taken by the user the medication chamber may be formed such that its volume is small. This may be realized by placing the mesh close to the vibration source such that they are separated from each other by a small gap. The gap should still be large enough to enable the vibration source to cause in use a standing wave in the liquid filled medication chamber. For efficient operation of the nebulizer the dimension of the gap, the distance between the mesh and the vibration source, should be approximately n*Lambda/2 [m], wherein Lambda=v/f, v being the speed of a wave [m/s] in the medication liquid caused by the vibration at a frequency f [Hz] and n being an integer larger than 0. For efficient operation and a medication chamber with a small volume n is chosen in the range of 1 to 3.

When the head is coupled to the body an electrical coupling between them is established to enable energy transfer from the body to the head and signal transfer from the head to the body. This electrical coupling may be realized with metal elements that contact each other when the head is coupled to the body. However a frequent cleaning of the head may result in a decreased contact quality for example because of oxidation of the metal. Or steam may enter the head through minuscule channels between the metal and the plastic housing of the head. In a further embodiment of the nebulizer the electrical coupling between the body and the head is realized with a magnetic field coupling between the head and the body.

The head may comprise a receiver coil electrically coupled to the vibration source and the body may comprise a transmitter coil coupled to an AC current or AC voltage source, the receiver and transmitter coil being aligned such that when the head is attached to the body the transmitter and receiver coil are magnetically coupled. An AC current in the transmitter coil causes a magnetic field which on its turn causes a current in the receiver coil, thereby providing a wireless powering of the head.

To optimize the magnetic field coupling between the head and the body a split transformer may be used. The split transformer comprises a core which is split in at least two parts. The first part is included in the head; the second part is included in the body. Each of these two core parts has its corresponding winding. When the head is attached to the body the two core parts align and the split transformer operates as a transformer having a core with two air splits.

As an example each part of the split core may have a U shape. When the head is attached to the body the ends of the legs of the two U shaped cores face each other and have an air gap between them. The receiver and transmitter coils each are wound around their respective U shaped core. Other shaped cores like an E shape may also be used to have for example two pairs windings on the split transformer. A first pair comprises a primary winding at a first E core on the transmitter side in the body and a secondary winding at a second E core at the receiver side in the head and may be used to transfer a drive signal and energy for the vibration source. A second pair comprising a further primary winding at the first E core and a further secondary winding on the second E core may be used to transfer energy for a flow sensor supply which is included in the head to power the flow sensor circuitry.

In the head the receiver coil may be coupled to the vibration source, which for example is a piezo electric element. The number of windings of the receiver and transmitter coil may be different to obtain a predetermined driving voltage for the piezo electric element. In this embodiment the frequency of the AC current corresponds to the vibration frequency of the piezo.

In a further embodiment the frequency of the AC current is chosen above 1 MHz to obtain small dimensions for the split transformer and a narrow gap of approximately Lambda/2 [m] between the mesh and the vibration source to obtain medication chamber with a small volume.

The signal from the flow sensor may be transferred from the head to the body with a magnetic field and/or optical coupling between the head and the body.

In yet a further embodiment the nebulizer comprises communication means to provide a data exchange with a personal computer (PC), the PC and the nebulizer together forming the nebulizing system. The coupling between the nebulizer and the personal computer may be wireless or wired, for example with a USB coupling. Flow data dependent on the signal from the sensing means may be transmitted by the communication means from the nebulizer to the PC. Said flow data may be used to train the person in the use of the nebulizer. For example the nebulizer or the PC may give an instruction to the person to inhale and/or exhale with his mouth coupled to the mouthpiece of the nebulizer such that his inhaled and/or exhaled breath causes a flow through the air channel. A programmed algorithm running on the PC interprets the received flow data and gives visual and/or audible feedback to the person such that the person is trained before the person starts using the nebulizer with medicine liquid.

In a further embodiment the visual and/or audible feedback is given by the nebulizer itself, the algorithm interpreting the signal from the flow sensor being implemented on the processor which is included in the nebulizers' body.

The invention further provides a method of detecting the inhaled or exhaled breath of the person using a nebulizer. The method includes the step of measuring the flow in the air channel with sensing means in the detachable head, the flow being caused by the inhaling or exhaling of the person. While breathing the air channel is coupled with the mouthpiece to the mouth of the person causing the flow through the air channel.

Any additional features can be added, some are described in more detail below. Any of the additional features can be combined together and combined with any of the aspects, as would be apparent to those skilled in the art. Other advantages will be apparent to those skilled in the art, especially over other prior art. Numerous variations and modifications can be made without departing from the claims of the present invention. Therefore, it should be clearly understood that the form of the present invention is illustrative only and is not intended to limit the scope of the present invention.

BRIEF DESCRIPTION OF THE DRAWINGS

How the present invention may be put into effect will now be described by way of example with reference to the appended drawings, in which:

FIG. 1 shows an embodiment of a nebulizer according to the invention;

FIG. 2 shows an embodiment of an air channel;

FIG. 3 shows an embodiment of an integrated circuit;

FIG. 4 shows an air channel with a thermal flow sensor;

FIG. 5 shows a further embodiment of a nebulizer.

The drawings described are only schematic and are non-limiting. In the drawings, the size of some of the elements may be exaggerated and not drawn on scale for illustrative purposes.

DETAILED DESCRIPTION OF THE EMBODIMENTS

The present invention will be described with respect to particular embodiments and with reference to certain drawings but the invention is not limited thereto but only by the claims.

FIG. 1 shows a nebulizer 10 comprising a head 20 and a body 30 wherein the head is detachable from the body to facilitate for example steam cleaning of the head after use. The body comprising controlling means 60, 62 may be rinsed to clean it. Steam cleaning is not necessary as the body has no direct contact with a medication liquid or inhaled 5 or exhaled 7 breath. This is advantageous for the expected lifetime of the body as the steam can have a detrimental effect on electronic circuits such as the controlling means that are included in the body. The head comprises a medication chamber 40, a vibration source 44 such as a piezo electric element, a mesh 42 and an air channel 50. The vibration source is activated by the driving circuit 60 to cause a standing wave in the liquid. The liquid may for example comprise a medication dissolved in water and is also referred to as medication liquid. The standing wave between the vibration source and the mesh causes the ejection of droplets in the air channel. The air channel ends at one side in a mouthpiece 70 and at the other side in an ambient port 51 which is in open contact with ambient air. A user puts the mouthpiece 70 against his mouth and inhales 5 and exhales 7 causing a flow through the air channel. The inhaling and exhaling is detected by the sensing means 52 and an output of the sensing is coupled to the controlling means 60, 62. A signal 54 indicative of the inhaling and exhaling is used by the controlling means to synchronize the driving circuit 60 with the breathing such that for example during exhaling the nebulizing of the medication liquid is interrupted. To allow cleaning the head can be opened, for example along line 43, to allow access to the interior of the air channel as well as to the mesh 42. The mesh is detachable from the medication chamber such that also the interior of the medication chamber may be cleaned. A further advantage of a detachably coupled mesh is that it can be replaced when its performance has worsened for example because a predetermined percentage of the plurality of holes in the mesh has become obstructed.

When the head is coupled to the body an electrical connection between the piezo driving circuit 60 and the vibration source 44 and between the flow sensor 52 and a processor 62 is obtained. The processor determines the driving frequency and duty cycle of a driving signal 45 which is provided by the driving circuit 60 to the vibration source 44. The electrical coupling may be realized with a "plug-socket" type of connection. For durability and reliability it may be advantageous to have a magnetic field coupling which is discussed later. The processor 62 and the sensing means 52 may further have an optical coupling which does not suffer from a possible interference caused by the magnetic field.

In FIG. 1 the nebulizing means may comprise a cylindrical shaped medication chamber 40 having a detachably coupled mesh at one side and a piezo electric element glued to it at the other side. The volume of the medication chamber is preferably small to prevent that a relative large amount of left medicine needs to be removed when cleaning the head. The volume can be minimized by reducing the distance or gap between the mesh and the piezo electric element. However to obtain a standing wave between the piezo electric element and the mesh the distance should not be smaller than approximately $\lambda/2$ [m], wherein $\lambda$ is the wavelength. The wavelength is dependent on the frequency of the vibration and the propagation speed in the medicine. For efficient operation and a medication chamber with a small volume the distance between the mesh and the piezo electric element is approximately $\lambda/2$ [m], $\lambda$ [m] or $3\lambda/2$ [m]. In a further embodiment of the nebulizing means the mesh 42 has a concave shape to obtain an improved dispersion of the cloud of droplets in the air channel.

In the invention the flow caused by an inhaling or exhaling user is detected by sensing means 52 which are included in the head 20 of the nebulizer. In a further embodiment the sensing means 52 are positioned to detect the flow in a portion of the air channel 50 between the medication chamber 40 and the ambient port 51 which has a smaller cross section than a further portion of the air channel between the medication chamber and the mouthpiece 70. By measuring the flow in the narrower portion of the air channel the signal 54 from the sensing means provides a better representation of the actual flow in the air channel. Further the value of the flow will be higher in the narrower portion thereby enhancing the sensitivity of the flow measurement.

The sensing means 52 may for example comprise a pressure sensor that measures the pressure in the air channel 50. The pressure changes during inhaling 5 or exhaling 7 of the user and therefore the pressure sensor enables the detection of the flow in the air channel.

In a further embodiment the sensing means may comprise a flow sensor. The flow sensor may for example comprise a valve that moves as a result of the flow in the air channel. The movement of the valve may be used to distinguish between an inhaling and exhaling breath.

In a further embodiment the flow sensor comprises a thermal element and senses the flow caused by the inhaled and exhaled breath based on a temperature measurement. Such a flow sensor is referred to as a thermal flow sensor device and has the advantage of not comprising any moving parts.

FIG. 1 further shows a nebulizing system comprising the nebulizer 10 and a personal computer (PC) 92. The nebulizer comprises communication means 90 which enable a data exchange with the personal computer 92. In an embodiment of the system the user may couple the nebulizer with a USB cable 91 to his PC. The coupling may however also be wireless. A program on the PC may be used to train the person in the use of the nebulizer. For example the user may need to be trained in inhaling and exhaling having the nebulizer pressed against his mouth. In the training method the person is asked to inhale and exhale through air channel 50 of the nebulizer. The instruction for inhaling 5 and/or exhaling 7 may be shown on the screen of the PC. The sensing means 52 measure the flow caused by the inhaling and exhaling of the person and data corresponding to the measured flow is transmitted with the communication means 90 to the PC. In response to the received data feedback is given to the person. This feedback may comprise further instructions such as for example to breathe slower or deeper.

In a further embodiment the training method is implemented in the processor 62 of the nebulizer 10. The instructions to the person may be given audible. Feedback may also be given audible, for example in terms of a sound indicating a pass when the inhaling and exhaling complied with predetermined criteria or a fail when during the training the breathing did not comply with the predetermined criteria. In a further embodiment feedback is given visually for example on a LCD screen on the nebulizer body 30. The LCD screen may display for example further instructions to breathe slower or deeper.

FIG. 2 shows a portion of the air channel 50. The inhaled 5 and exhaled 7 breath cause a flow through the air channel which is detected with a thermal flow sensor device 53. The thermal flow sensor device may for example be positioned in a recess in the wall 58. The thermal flow sensor device has a front side 8. After use the air channel may be cleaned by opening the head as discussed earlier. To prevent any residue the surface of the flow sensor device preferably matches with the wall 58 surrounding it to obtain a smooth interior in the air channel. The thermal element on the flow sensor device may comprise a thermal heating element 56*a* and two thermal sensor elements 56*b* surrounding it. In case there is no flow the two thermal sensor elements 56*b* will both measure approximately the same temperature. In case the left thermal sensor element measures a higher temperature than the right thermal sensor element the flow must be from right to left as the flow transports the heat produced by the thermal heating element 56*a* causing a small rise in temperature of the left thermal sensing element. Hence the detected flow was caused by an inhaling breath 5 of the user. Likewise the exhaling is detected by the thermal flow sensor device.

In a further embodiment the flow sensor detects not only the direction of the flow in the air channel but also its rate. When a detected rate is above or below a predetermined threshold the controlling means may give a warning to the user. In a further embodiment the nebulizer may be put in a training mode in which no atomization of the medicine takes place and the user is instructed to inhale and exhale whereby the controlling means give a warning when the inhaling or exhaling is causing a too large or too small flow for the nebulizer to work effectively.

FIG. 3 shows a cross section of a portion of a processed integrated circuit 130 that is part of the thermal flow sensor device 53. Facing upwards is the component side comprising a polysilicon (PS) resistor 300 that is connected with a metal track 600. On top of the polysilicon resistor other layers may be formed such as a further metal layer 750 which can be used to tune thermal conductivity. The metal track 600 contacts the substrate 200 through a contact hole (CO) and after the back side etching of the substrate the backside (the side facing downward) of the metal track is accessible and forms a bonding area or bondpad 160 at the backside of the die. With the shown bonding at the bondpad 160 a connection with one of the two terminals of the PS resistor is realized.

Before the etching of the substrate takes place the die is connected via a glue layer 1000 to an electrical insulating substrate 900 such as glass. The thin layer (typically 400 micrometer) of glass provides a good thermal conductivity to the PS resistor. Further the glass layer provides mechanical stability to the die to enable the etching through the substrate to the metal track.

The integrated circuit 130 further comprises thermal sensing elements surrounding the heating element. A temperature difference between any two thermal sensing elements may be used to determine the flow direction in the air channel. The thermal sensing element may for example comprise a PN junction of which the forward voltage is dependent on temperature. In a further embodiment the thermal sensing element comprises a string of thermocouples, each thermocouple comprising a polysilicon-metal junction. This provides the advantage that no additional layers and processing is required to obtain the thermal sensing element as it is made in the same process steps as the polysilicon resistor 300 and the metal track 600 and can be connected from the backside in the same way as the PS resistor as discussed earlier.

In a further embodiment the thermal flow sensor device 52 in the air channel 50 is calibrated using a predetermined flow with a known direction and rate. The detected temperature differences sensed by the thermal sensing elements are stored in a look up table. The look up table may for example be stored in a memory comprised in the controlling means 60, 62. In use the temperature differences sensed by the thermal flow sensor device 53 are compared with stored values from the look up table to determine the flow rate in the air channel.

The above discussed calibration method is also applicable for other sensing means such as a pressure sensor.

FIG. 4 shows a further cross section of a portion of a processed integrated circuit 130 with a different implementation of the back side contacting. As in FIG. 3 the thermal heating element is realized with a PS resistor 300 that is connected to a metal track 600. The substrate 200 in this implementation is however highly doped and therefore low resistive. As discussed earlier the wafer (containing a plurality of the dies) is bonded (using glue 1000) to a glass layer 900. The backside of the wafer obtains a metal layer 210 on the substrate and is subsequently etched resulting in "electrically isolated pillars" 240 to remain. Shown is a pillar 240 that connects via the metal track 600 to a terminal of the PS resistor 300. The metal on the pillars forms bondpads and can be contacted with wire bonding or can be connected to pads on a printed circuit board (PCB) 290 using stud bumps. An adhesive 330 is applied between the PCB and the integrated circuit die 130 to prevent penetration of dirt or vapor. The thermal flow sensor device comprises the assembly of the integrated circuit 130 die and the PCB 290. The assembly is mounted in a window in the wall 58 of the air channel and sealed to prevent leakage. The glass layer 900 faces the interior of the air channel. In a further embodiment the wall 58 has a locally thinned part in which the assembly is fitted such that the thinned part separates the integrated circuit die from the interior of the air channel. The thinned part provides an improved barrier to reduce a risk of leakage or contamination.

Figure 5:
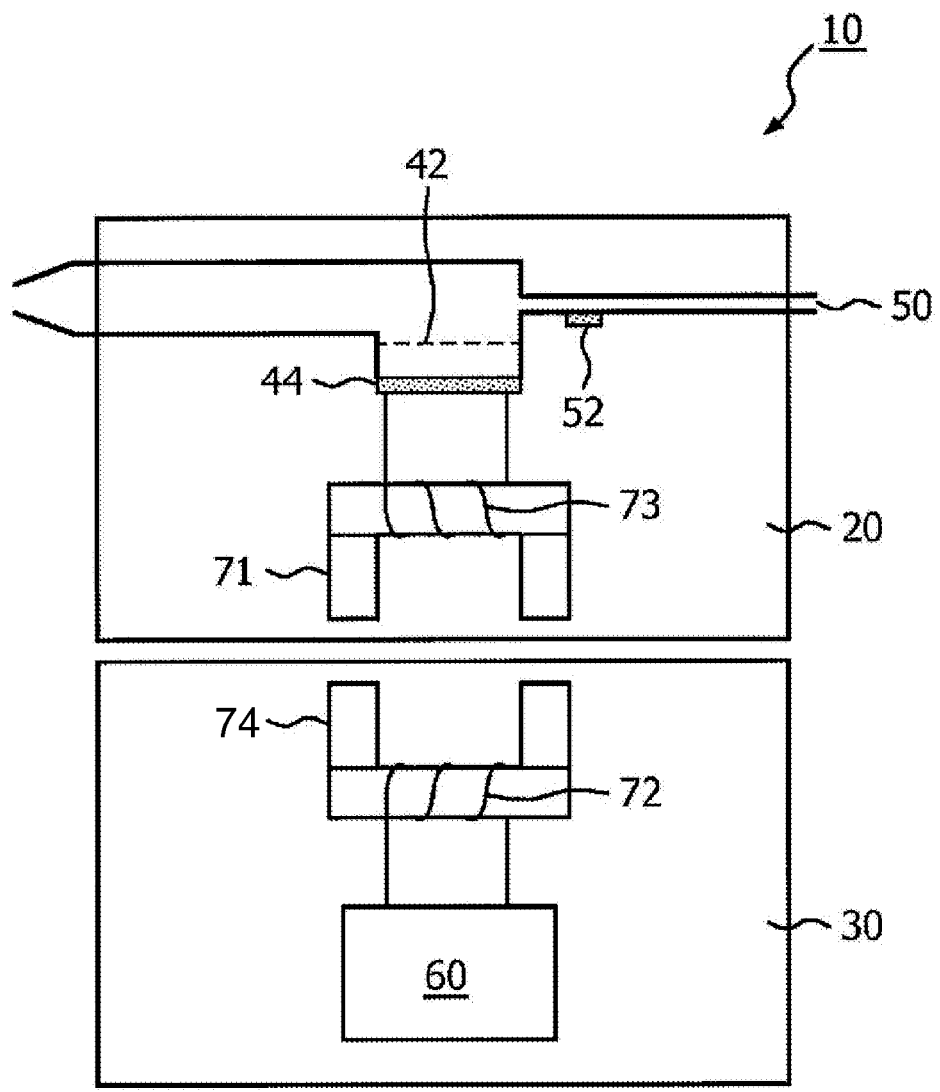

FIG. 5 shows a further embodiment of the nebulizer in which only those parts relevant for the discussion are shown. In this embodiment the driver circuit 60 activates the vibration source 44 using a magnetic field coupling between the body 30 and the head 20. This provides the advantage that no electrical contacts are accessible at the exterior of the head and the body. Electrical contacts at the exterior may damage due to frequent decoupling of the head and the body or by frequent steam cleaning of the head. The magnetic field coupling comprises two U shaped cores 70, 71 of which the legs are aligned when the head is detachably coupled to the body. When aligned the two U shaped cores make up a split transformer having a primary winding 72 coupled to the driving circuit 60 and a secondary winding 73 coupled to the vibration source 44, which for example is a piezo electric element. The winding ratio of the secondary and primary winding can be used to obtain a predetermined driving voltage for the piezo electric element. The frequency of a current provided by the driving circuit 60 and passing through the primary winding 72 determines the vibration frequency and hence can be used to control the nebulizing of the liquid in the medication chamber. To obtain small dimensions for the split transformer the driving circuit should provide a relative high frequent (e.g. above 1 MHz) AC drive current through the primary winding 72. Having the secondary winding 73 driving the piezo electric element 44 said relative high frequency may further be used to provide the additional advantage of a relative narrow minimal gap of $\lambda/2$ [m], $\lambda$ [m] or $3\lambda/2$ [m] between the piezo electric element 44 and the mesh 42 resulting in the medication chamber having a relative small volume.

In a further embodiment the sensing means included in the nebulizers' head 20 is implemented as a thermal flow sensor device 52 or MEMS pressure sensor mounted in a recess of the air channel. The supply for the sensing means is also obtained with a magnetic field coupling between the head and the body. The split transformer comprises an additional secondary winding for powering the sensing means.

In a further embodiment the split transformer comprises two E shaped cores. The split transformer may have an additional primary winding coupled with a magnetic field coupling to the additional secondary winding. The additional primary and secondary windings for providing energy to the sensing means are each made across the center leg of its corresponding E shaped core whereas the primary and secondary winding for the piezo drive are arranged on the outer legs of the E shaped core. This arrangement provides a separation between the primary winding and the additional primary winding, and between the secondary and additional secondary winding resulting in a reduced interference.

Where an indefinite or definite article is used when referring to a singular noun e.g. "a" or "an", "the", this includes a plural of that noun unless something else is specifically stated.

The term "comprising", used in the claims, should not be interpreted as being restricted to the components listed thereafter; it does not exclude other elements or steps. Thus, the scope of the expression "a device comprising components A and B" should not be limited to devices consisting only of components A and B. It means that with respect to the present invention, the only relevant components of the device are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The invention claimed is:

1. A nebulizer comprising;

a head, the head comprising;

a medication chamber configured to hold medicament as a body of liquid, a vibration source configured to apply vibrational energy to a medicament within the medication chamber in order to nebulize the medicament, such vibrational energy being applied to the medicament while the medicament is held as a body of liquid in the medication chamber, an air channel in which the nebulized medicament is released, the air channel being arranged to guide a flow caused primarily by respiratory effort of a user during an inhaled and exhaled breath of the user; and a sensor configured to generate output signals that convey information related to a direction of the flow; and a body detachably coupled to the head, the body comprising a controller to control operation of the vibration source between different non-zero frequencies for different directions of the flow.

2. A nebulizer according to claim 1 wherein the medication chamber for holding the liquid comprises the vibration source arranged to transfer vibrations to the liquid, wherein the vibration source includes a mesh, wherein the air channel is arranged to guide the flow along the mesh.

3. A nebulizer according to claim 2 wherein the mesh is detachably coupled to the medication chamber.

4. A nebulizer according to claim 2 wherein the medication chamber is formed such that the mesh is separated from the vibration source by a gap, the vibration source being arranged to vibrate at a frequency f, the mesh being separated from the vibration source by the gap forming a distance between the mesh and the vibration source of substantially Lambda/2, wherein Lambda=v/f, v being the speed of a wave in the liquid caused by the vibration at frequency f.

5. A nebulizer according to claim 2 wherein an electrical energy source is arranged to transfer energy from the body to the head to energize the vibration source and/or the sensor, wherein the sensor comprises a flow sensor using a magnetic field coupling between the head and the body.

6. A nebulizer according to claim 5 wherein the head further comprises a receiver coil, the body further comprises a transmitter coil, the receiver coil being electrically coupled to the vibration source, the body being arranged to cause an AC current in the transmitter coil so as to energize the vibration source when the head is coupled to the body.

7. A nebulizer according to claim 6 wherein the transmitter coil is arranged to surround a first magnetic core, the receiver coil is arranged to surround a second core, the first and second core being U shaped or E shaped, the ends of the first and second core being arranged to face each other when the head is coupled to the body.

8. A nebulizer according to claim 6 wherein the AC current has a frequency corresponding to the vibration frequency f.

9. A nebulizer according to claim 8 wherein the frequency f is higher than 1 MHz.

10. A nebulizer according to claim 2 wherein the vibration source comprises a piezo electric element.

11. A nebulizer according to claim 1 wherein, operation of the controller is dependent on a signal received from the sensor.

12. A nebulizer according to claim 11 wherein the controller is arranged to energize the vibration source in dependence of the signal received from the sensor.

13. A nebulizer according to claim 12 wherein the signal corresponds to a direction of the flow in the air channel.

14. A nebulizer according to claim 1 wherein the sensor comprises a pressure sensor arranged to sense the flow based on a pressure measurement.

15. A nebulizer according to claim 1 wherein the sensor comprises a flow sensor arranged to sense the flow in the air channel.

16. A nebulizer according to claim 15 wherein the flow sensor is a thermal flow sensor device arranged to sense the flow based on a temperature measurement.

17. A nebulizer according to claim 15 wherein a thermal flow sensor device comprises an electrically driven thermal element on a front side of the thermal flow sensor device, the front side facing the interior of the air channel.

18. A nebulizer according to claim 17 wherein the thermal flow sensor device comprises an integrated circuit die, the integrated circuit die further comprising the electrically driven thermal element on the front side and one or more bondpads at its backside, the one or more bondpads being electrically coupled to the thermal element.

19. A nebulizer according to claim 17 wherein the thermal element comprises a heating element and at least two temperature sensing elements.

20. A nebulizer according to claim 19 wherein the heating element comprises a resistor.

21. A nebulizer according to claim 19 wherein the temperature sensing element comprises a thermocouple.

22. A nebulizer according to claim 17 wherein the air channel comprises a wall, the wall having a recess in which the thermal flow sensor device is mounted with the electrically driven thermal element facing the air channel.

23. A nebulizer according to claim 1 wherein the sensor comprises a flow sensor, and a signal from the flow sensor is transferred from the head to the body with a magnetic field and/or optical coupling between the head and the body.

24. A nebulizing system comprising a nebulizer according to claim 1 and a personal computer, wherein the nebulizer further comprises a communication system configured for a data exchange with the personal computer.

25. A nebulizing system according to claim 24 wherein the communication system is configured for a wireless coupling of the nebulizer and the personal computer.

26. A nebulizing system according to claim 24 wherein the data exchange includes flow data, the flow data being dependent on the signal.

27. The nebulizer of claim 1, wherein the controller controls the vibration source (i) to operate at a first non-zero frequency while the direction of the flow indicates inhalation of the user, and (ii) to operate at a second non-zero frequency while the direction of the flow indicates exhalation of the user.

28. A method of nebulizing, the method comprising;
holding medicament as a body of liquid within a medication chamber within a head of a nebulizer;
generating vibrational energy with a vibrational source disposed within the head of the nebulizer to nebulize the liquid medicament, wherein the vibrational energy is provided to the medicament while the medicament is held as a body of liquid in the medication chamber;
generating, with a sensor disposed within the head of the nebulizer, output signals that convey information related to a direction of flow in an air channel of the nebulizer;
the air channel being configured to guide a flow of nebulized medicament being caused primarily by respiratory effort of a user during the users inhaled and/or exhaled breath;

controlling a frequency of vibration of the vibration source between different non-zero frequencies with a controller disposed in a body of the nebulizer that is detachably coupled to the head, the controlling is performed so that different the vibration source operates at different non-zero frequencies for different directions of flow in the air channel.

29. The method of claim 28 further comprising controlling the nebulizer in dependence of a signal received from the sensor.

30. A method of training a person in the use of a nebulizer, the method comprising the method of claim 28 and further comprising: providing an instruction to the person to inhale and/or exhale, and providing audible and/or visual feedback to the person on his inhaling and/or exhaling in dependence of a signal received from the sensor.

31. A method of training a person in the use of a nebulizer according to claim 30 wherein the audible and/or visual feedback is provided on a personal computer which is coupled to the nebulizer for data exchange.

* * * * *